US011565237B2

(12) United States Patent
Kevlahan et al.

(10) Patent No.: US 11,565,237 B2
(45) Date of Patent: *Jan. 31, 2023

(54) COMPOSITIONS, DEVICES, AND METHODS FOR CELL SEPARATION

(71) Applicant: QT Holdings Corp, Woburn, MA (US)

(72) Inventors: Sean H. Kevlahan, North Reading, MA (US); Andrew Ball, Georgetown, MA (US); Guokui Qin, Somerville, MA (US); Steven B. Wells, Allston, MA (US)

(73) Assignee: QT Holdings Corp, Woburn, MA (US)

(*) Notice: Subject to any disclaimer, the term of this patent is extended or adjusted under 35 U.S.C. 154(b) by 1171 days.

This patent is subject to a terminal disclaimer.

(21) Appl. No.: 16/086,267

(22) PCT Filed: Mar. 20, 2017

(86) PCT No.: PCT/US2017/023207
§ 371 (c)(1),
(2) Date: Sep. 18, 2018

(87) PCT Pub. No.: WO2017/161371
PCT Pub. Date: Sep. 21, 2017

(65) Prior Publication Data
US 2019/0336940 A1 Nov. 7, 2019

Related U.S. Application Data

(60) Provisional application No. 62/310,360, filed on Mar. 18, 2016.

(51) Int. Cl.
B01J 20/24 (2006.01)
C12N 5/0783 (2010.01)
(Continued)

(52) U.S. Cl.
CPC .......... *B01J 20/24* (2013.01); *B01D 15/3809* (2013.01); *B01J 20/28004* (2013.01);
(Continued)

(58) Field of Classification Search
None
See application file for complete search history.

(56) References Cited

U.S. PATENT DOCUMENTS 5,167,811 A 12/1992 Graves et al.
7,214,245 B1 5/2007 Marcolongo et al.
(Continued)

FOREIGN PATENT DOCUMENTS

WO WO1986003136 A1 6/1986
WO WO1996028029 A1 9/1996
(Continued)

OTHER PUBLICATIONS

Chihiro Miyajima, "General Information on Alginates and their Applications" Seni Gakkaishi (Fiber and Industry) vol. 65. No. 12 (2009), P444.
(Continued)

Primary Examiner — Joseph D Anthony
(74) Attorney, Agent, or Firm — Anne M. Reynolds; Casimir Jones, S.C.

(57) ABSTRACT

The invention features a substrate and compositions, kits, devices, and methods employing the substrate that produces an isolated population of cells from a general population. The isolated population is enriched for one or more target populations. Substrate is can be liquefied and allows recovery of unlabeled, viable, and functional cells.

17 Claims, 9 Drawing Sheets

(51) Int. Cl.
  *B01J 20/28* (2006.01)
  *B01D 15/38* (2006.01)

(52) U.S. Cl.
  CPC ... *B01J 20/28016* (2013.01); *B01J 20/28047* (2013.01); *B01J 20/28085* (2013.01); *C12N 5/0636* (2013.01)

(56) References Cited

U.S. PATENT DOCUMENTS

| | | | |
|---|---|---|---|
| 9,790,467 B2* | 10/2017 | Kevlahan | C07K 16/2818 |
| 10,620,212 B2 | 4/2020 | Miltenyi et al. | |
| 2009/0087346 A1 | 4/2009 | Luchini et al. | |
| 2012/0061305 A1 | 3/2012 | Quake et al. | |
| 2015/0160237 A1 | 6/2015 | Wiencierz et al. | |
| 2015/0322407 A1* | 11/2015 | Firpo | A61K 35/39 |
| | | | 435/377 |
| 2018/0171296 A1* | 6/2018 | Murthy | C12N 5/0018 |
| 2020/0085971 A1* | 3/2020 | Kevlahan | C07K 16/28 |

FOREIGN PATENT DOCUMENTS

| | | |
|---|---|---|
| WO | WO 2009-018544 | 2/2009 |
| WO | WO2010132795 A2 | 11/2010 |
| WO | WO 2012-068243 | 5/2012 |
| WO | WO 2012-106658 | 8/2012 |
| WO | WO 2015-148512 | 10/2015 |

OTHER PUBLICATIONS

Arya et al., "Capturing rare cells from blood using a packed bed of custom-synthesized chitosan microparticles," J. Mater. Chem. B, 1, 2013, 4313-4319.

Extended European Search Opinion for European Application No. EP17767702.8 (7 pages).

International Search Report and Written Opinion, PCT/US2017/023207, (11 pages).

Pierzchalski et al., "An Innovative Cascade System for Simultaneous Separation of Multiple Cell Types," PLOS One, 8:9, 2013, 1-9.

Hall et al., Microencapsulation of islets within alginate/poly(ethylene glycol) gets cross-linked via Staudinger ligation, Acta Biomater. 2011;7(2):614-24.

Laurienzo et al., Synthesis and characterization of a novel alginate-poly (ethylene glycol) graft copolymer. Carbohydrate Polymers. 2005; 62(3):274-282.

* cited by examiner

FIGURES 6A-6B
Figure 6A
Isolation of CD34+ Kg1A cells
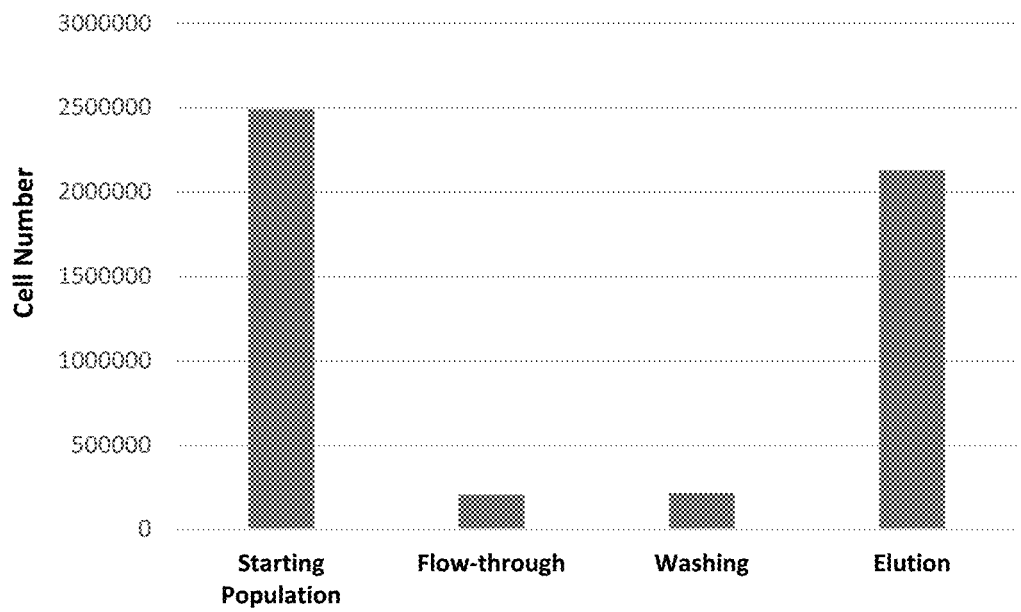
Figure 6B
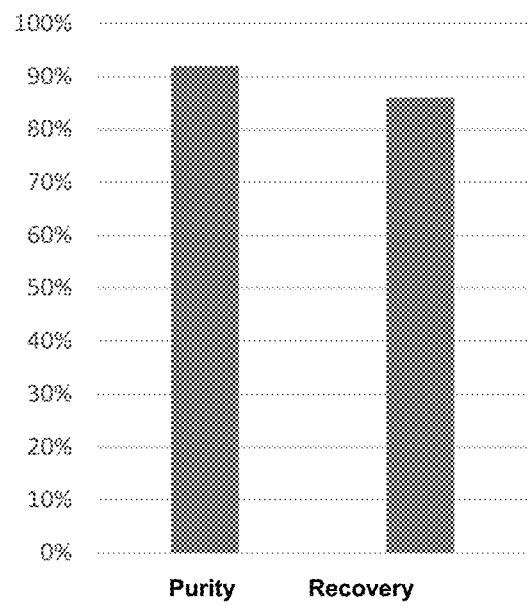

FIGURES 7A-7C
Figure 7A
Starting PBMC
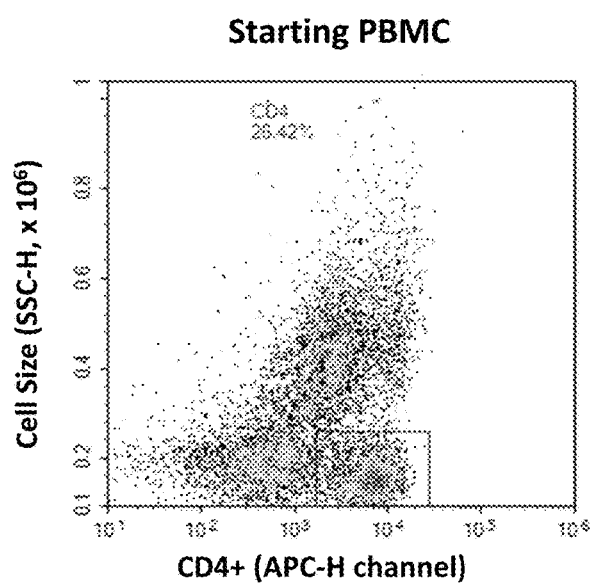
Figure 7B
Purified CD4+ T cells
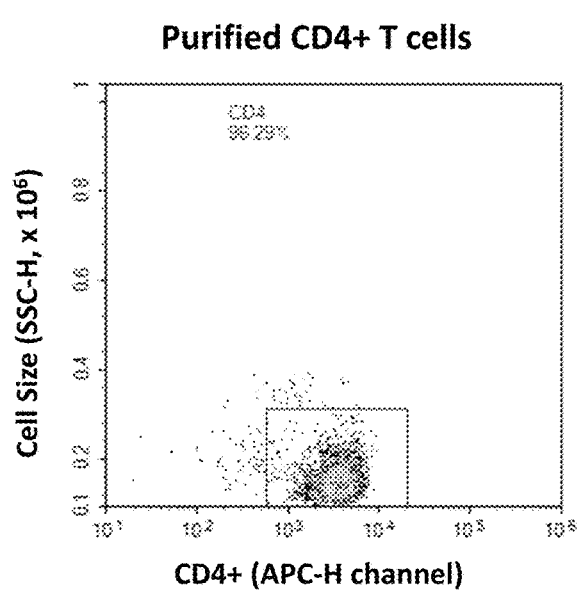
Figure 7C
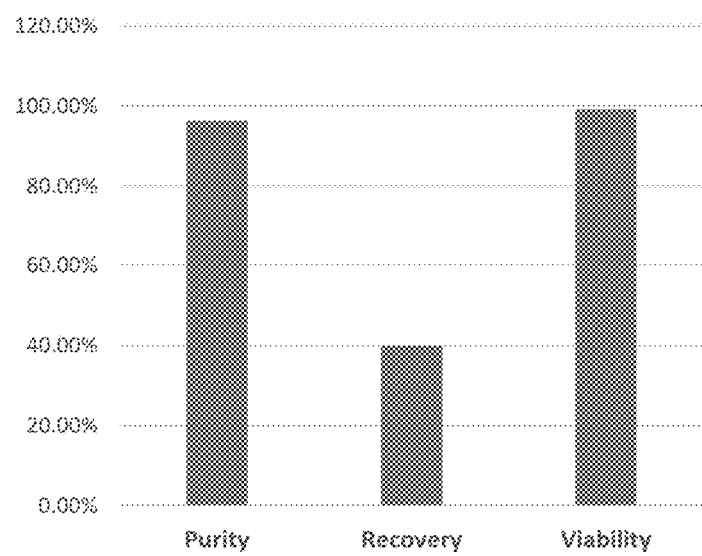

FIGURES 8A-8C
Figure 8A
Starting PBMC
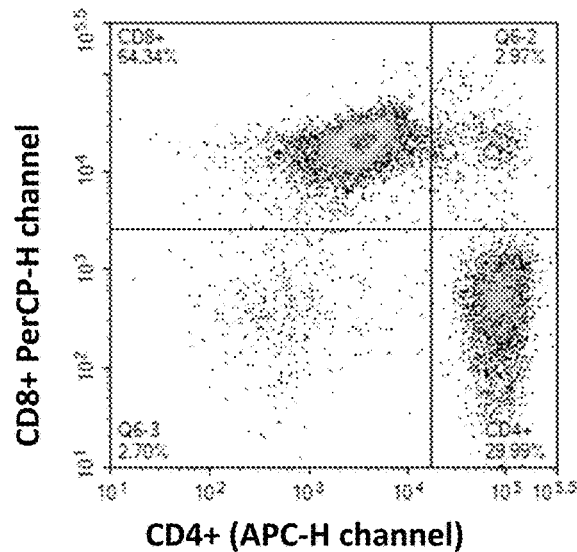
Figure 8B
Purified CD8+ T cells
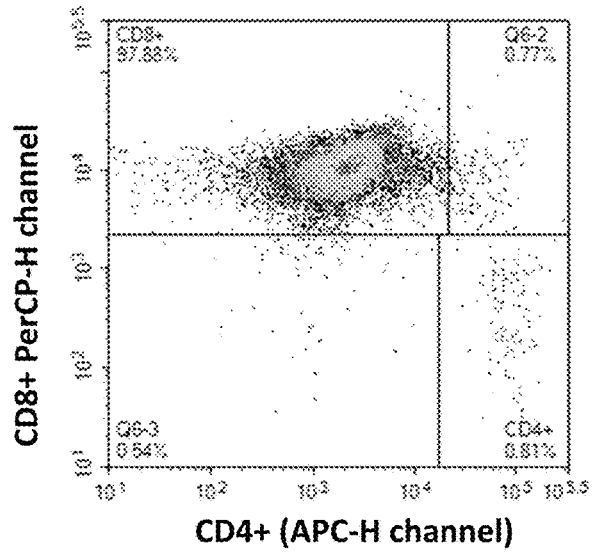
Figure 8C
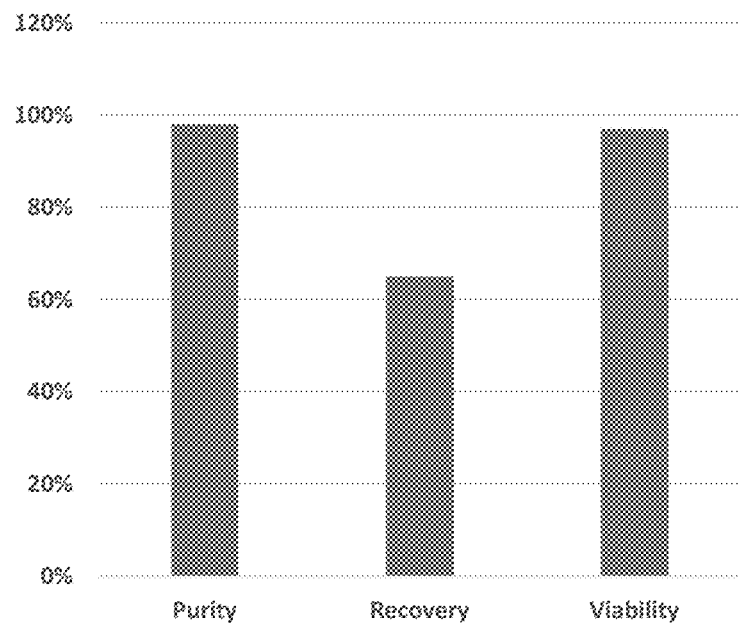

COMPOSITIONS, DEVICES, AND METHODS FOR CELL SEPARATION

FIELD OF THE INVENTION

The invention is generally directed to the field of cell separation, cell culture, and bioprocessing. More specifically, the invention is directed toward improved protocols for isolating or enriching for specific subpopulations of cells for research or clinical applications.

BACKGROUND

Cell-based therapies promise to transform healthcare in the coming decades, offering breakthrough treatments for cancer, diabetes, and numerous other diseases impacting patients globally. However, to realize this potential, a method for producing functional cells in a safe and economically viable manner is needed. The enrichment of a target cell population, and subsequent cultivation of desired cells from a defined cell population, is an important first step in many complex biologic and biomedical workflows. Thus, improved cell enrichment processes will contribute to an overall simplified experimental protocol in the fields of fundamental biological research, tissue engineering, regenerative medicine, and diagnostics/therapeutic health monitoring. The production of advanced cell-based therapeutics requires purification of cells on the basis of surface antigen expression, as such cells cannot be distinguished from others in the same source (e.g. blood or tissue) via physical parameters, such as size or density, alone. Purification of such cells therefore typically requires tagging with surface markers.

Current clinical laboratory and basic biology research applications face significant challenges in the isolation and study of target cells of interest, including: (1) difficulty in achieving high purity multi-marker-based cell isolation from a complex blend of non-target cells; (2) complex native environments with extremely heterogeneous populations, such as blood cells and bone marrow; (3) inaccurate analysis of blood character and condition required for isolation of a few desired cells; (4) inefficient large-scale cell enrichment for low starting cell concentrations in cases such as stem or progenitor cells; (5) effective sorting of two or more cell types with high cell viability to support numerous biomedical pursuits.

Currently, physical separation techniques are commonly used for pre-purification and concentration but have low specificity and are difficult to process on a large scale. Magnetic separation is expensive, slow, and laborious. In cases requiring positive selection techniques, magnetic separation leaves residual magnetic beads attached to purified cells and can impede proliferation and reduce viability. These residual beads ultimately reduce cell efficacy in transplantation and engraftment applications.

There is a need for effective cell separation techniques that deliver high cell purity and yield while maintaining cell function.

SUMMARY OF THE INVENTION

We have developed an efficient affinity chromatography cell sorting system that can purify multiple cell types with high purity and yield with minimal functional impact on purified cell populations. The invention adapts a unique biocompatibly dissolvable hydrogel for use in an affinity chromatography system, enabling positive selection without residual affinity tags (e.g., immunofluorescent or magnetic tags).

In one aspect, the invention features a kit including a substrate, e.g., a porous substrate, attached to a binding unit configured to bind a surface of a target cell, wherein all or a portion of the substrate liquefies upon decreased availability of a crosslinking agent; and a strainer, e.g., housing in a container, through which cells can pass but the substrate cannot. In certain embodiments, the kit further includes a chelator for a cation that crosslinks the substrate, such as EDTA, EGTA, sodium citrate, BAPTA, crown ether, cryptand, phenanthroline sulfonate, dipyridyl sulfonate, dioxane, DME, diglyme, or triglyme. The substrate may include microbeads, e.g., having a diameter from 1-1000 μm, such as 2-500 μm, 3-200 μm, 4-100 μm, or 5-20 μm. In certain embodiments, the microbeads have a polydispersity index of 1-2. The binding unit is, for example, attached to the surface of the microbeads. The strainer may include a mesh or sieve and have a pore size of 1-1000 μm, e.g., 1-30 μm, 10-40 μm, 20-30 μm, 5-50 μm, 20-80 μm, 1-100 μm, 200-500 μm, or 500-1000 μm.

In certain embodiments, the substrate includes a crosslinkable polymer, such as a hydrogel. In other embodiments, the crosslinking agent is an ion, e.g., a cation, such as $Li^+$, $Mg^{2+}$, $Ca^{2+}$, $Sr^{2+}$, $Ba^{2+}$, $Zn^{2+}$, $Cu^{2+}$, or $Al^{3+}$, in particular $Ca^{2+}$. In further embodiments, the hydrogel includes alginic acid, e.g., in the form of an alginic acid-polyethylene glycol (PEG) copolymer. The hydrogel has, for example, a median viscosity of between about 0.01 and 400 centipoise (cP), e.g., about 80 cP.

The binding unit may include an antibody or antigen-binding fragment thereof, biotin, or a biotin binding protein. Examples of antibodies or antigen binding fragments thereof include a monoclonal antibody or antigen-binding fragment thereof, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')2) molecule, a domain antibody, a diabody, a triabody, an affibody, a domain antibody, a SMIP, a nanobody, a Fv fragment, a Fab fragment, a F(ab')2 molecule, or a tandem scFv (taFv) fragment. In certain embodiments, the binding unit binds one or more cell surface molecules selected from the group consisting of T cell receptor (TCR), CD3, CD4, CD8, CD11a, CD11b, CD11c, CD14, CD15, CD16, CD19, CD25, CD33, CD34, CD45RO, CD56, major histocompatibility complex (MHC), and chimeric antigen receptor (CAR).

In another aspect, the invention features a composition including a plurality of hydrogel microbeads, each attached to a binding unit configured to bind to a surface of a target cell, wherein the hydrogel microbeads have a diameter from about 1-1000 μm and wherein all of the hydrogel microbeads liquefy upon decreased availability of a crosslinking agent. The hydrogel microbeads may include alginic acid, e.g., in the form of an alginic acid-polyethylene glycol (PEG) copolymer. The hydrogel has, for example, a median viscosity of between about 0.01 and 400 centipoise (cP), e.g., about 80 cP. In certain embodiments, microbeads have a polydispersity index of 1-2. The binding unit is, for example, attached to the surface of the microbeads. In certain embodiments, the crosslinking agent is an ion, e.g., a cation, such as $Li^+$, $Mg^{2+}$, $Ca^{2+}$, $Sr^{2+}$, $Ba^{2+}$, $Zn^{2+}$, $Cu^{2+}$, or $Al^{3+}$, in particular $Ca^{2+}$. The binding unit may include an antibody or antigen-binding fragment thereof, biotin, or a biotin binding protein. Examples of antibodies or antigen binding fragments thereof include a monoclonal antibody or antigen-binding fragment thereof, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')2) molecule, a domain antibody, a diabody, a triabody, an affibody, a domain antibody, a SMIP, a nanobody, a Fv fragment, a Fab fragment, a F(ab')2 molecule, or a tandem scFv (taFv) fragment. In certain embodiments, the binding unit binds one or more cell surface molecules selected from the group consisting of T cell receptor (TCR), CD3, CD4, CD8, CD11a, CD11b, CD11c, CD14, CD15, CD16, CD19, CD25, CD33, CD34, CD45RO, CD56, major histocompatibility complex (MHC), and chimeric antigen receptor (CAR). The decreased availability may be caused by the presence of a chelating agent, such as EDTA, EGTA, sodium citrate, BAPTA, crown ether, cryptand, phenanthroline sulfonate, dipyridyl sulfonate, dioxane, DME, diglyme, or triglyme.

In a further aspect, the invention features a device including a container, e.g., including a column or trough, having an inlet and an outlet, the container containing a porous substrate and being configured to permit passage of cells from the inlet through the outlet while retaining the porous substrate within the container, wherein a binding unit configured to bind to a surface of a target cell is attached to the porous substrate, and wherein all or a portion of the porous substrate liquefies upon decreased availability of a crosslinking agent. In certain embodiment, the container includes a strainer, e.g., including a mesh or sieve, that permits passage of cells. The strainer may include a mesh or sieve and have a pore size of 1-1000 µm, e.g., 1-30 µm, 10-40 µm, 20-30 µm, 5-50 µm, 20-80 µm, 1-100 µm, 200-500 µm, or 500-1000 µm.

The porous substrate may be contained within a packed bed. In certain embodiments, the porous substrate includes a cross-linkable polymer, such as a hydrogel. In other embodiments, the crosslinking agent is an ion, e.g., a cation, such as $Li^+$, $Mg^{2+}$, $Ca^{2+}$, $Sr^{2+}$, $Ba^{2+}$, $Zn^{2+}$, $Cu^{2+}$, or $Al^{3+}$, in particular $Ca^{2+}$. In further embodiments, the hydrogel includes alginic acid, e.g., in the form of an alginic acid-polyethylene glycol (PEG) copolymer. The hydrogel has, for example, a median viscosity of between about 0.01 and 400 centipoise (cP), e.g., about 80 cP. The porous substrate may include microbeads, e.g., having a diameter from 1-1000 µm, such as 2-500 µm, 3-200 µm, 4-100 µm, or 5-20 µm. In certain embodiments, the microbeads have a polydispersity index of 1-2. The binding unit is, for example, attached to the surface of the microbeads.

The decreased availability may be caused by the presence of a chelating agent, such as EDTA, EGTA, sodium citrate, BAPTA, crown ether, cryptand, phenanthroline sulfonate, dipyridyl sulfonate, dioxane, DME, diglyme, or triglyme.

The binding unit may include an antibody or antigen-binding fragment thereof, biotin, or a biotin binding protein. Examples of antibodies or antigen binding fragments thereof include a monoclonal antibody or antigen-binding fragment thereof, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')2) molecule, a domain antibody, a diabody, a triabody, an affibody, a domain antibody, a SMIP, a nanobody, a Fv fragment, a Fab fragment, a F(ab')2 molecule, or a tandem scFv (taFv) fragment. In certain embodiments, the binding unit binds one or more cell surface molecules selected from the group consisting of T cell receptor (TCR), CD3, CD4, CD8, CD11a, CD11b, CD11c, CD14, CD15, CD16, CD19, CD25, CD33, CD34, CD45RO, CD56, major histocompatibility complex (MHC), and chimeric antigen receptor (CAR).

The device may further include one or more additional containers operatively connected to the outlet, wherein the one or more additional containers each includes a porous substrate having the same or different binding unit. The additional devices may be connected by one or more three-way valves.

In a related aspect, the invention features a method for separating a target cell by providing a suspension of cells including the target cell and non-target cells; contacting the suspension with a substrate to allow target cells to bind to the substrate, wherein a binding unit configured to bind to a surface of the target cell is attached to the substrate, and wherein all or a portion of the substrate liquefies upon decreased availability of a crosslinking agent; and removing unbound cells from the target cell bound to the substrate, e.g., in a container, thereby separating the target cell. In certain embodiments, the suspension and substrate are contacted prior to introduction into the container. Alternatively, the suspension and substrate are contacted in the container. The method may further include decreasing the availability of the crosslinking agent to liquefy the substrate, e.g., to release cells bound to the substrate.

In certain embodiments, the method produces a subpopulation including the target cell from the suspension. In some embodiments, the one or more target populations of cells accounts for at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) of the isolated population of cells. In some embodiments, the one or more target populations of cells accounts for 50% or less (e.g., 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1%, 0.01%, 0.001%, 0.0001%, 0.00001%, or less) of the general population of cells.

For any aspect of the invention, an exemplary target cell is a stem cell, circulating tumor cell, a cancer stem cell, or a white blood cell. For example, the target cell is a T cell, a T regulatory cell, a B cell, an NK cell, or a genetically engineered T cell, e.g., a chimeric antigen receptor T cell (CAR-T cell). Exemplary stem cells include undifferentiated or differentiated stem cells. A stem cell may be selected from the group consisting of a mesenchymal stem cell, a hematopoietic stem cell, an embryonic stem cell, and an induced pluripotent stem cell. In certain embodiments of any aspect of the invention, the target cells are bound to a second binding unit to which the binding unit of the substrate, e.g., porous substrate, or microbead binds.

The invention features a device including a column containing a porous substrate and a binding unit attached to the porous substrate. The binding unit is configured to bind to a surface of a target cell. All or a portion of (e.g., a surface layer of) the porous substrate liquefies upon decreased availability of a crosslinking agent. In some embodiments, the column further includes an inlet and an outlet, wherein the porous substrate is configured to permit passage of cells from the inlet to the outlet.

In some embodiments, the porous substrate includes a polymer (e.g., a cross-linkable polymer). In some embodiments, the polymer includes a hydrogel. In some embodiments, the hydrogel includes alginic acid or an alginic acid-polyethylene glycol (PEG) copolymer. In some embodiments, the hydrogel has a median viscosity from about 0.01 and about 400 cP when liquid. In some embodiments, the porous substrate consists of a plurality of microbeads. The microbeads can have a diameter from 1-1000 µm (e.g., 2-500 µm, 3-200 µm, 4-100 µm, or 5-20 µm) and/or a polydispersity index of 1-2 (e.g., as measured by gel permeation chromatography).

In some embodiments, the crosslinking agent is an ion (e.g., a cation, e.g., $Li^+$, $Mg^{2+}$, $Ca^{2+}$, $Sr^{2+}$, $Ba^{2+}$, $Zn^{2+}$, $Cu^{2+}$, or $Al^{3+}$). In some embodiments, the decreased availability is caused by the presence of a chelating agent. In some embodiments, the decreased availability is caused by the presence of EDTA, EGTA, sodium citrate, BAPTA, crown ether, cryptand, phenanthroline sulfonate, dipyridyl sulfonate, dioxane, DME, diglyme, or triglyme.

In some embodiments, the binding unit is attached to the porous substrate (e.g., the surface of the microbeads). In some embodiments, the binding unit includes an antibody or an antigen-binding fragment thereof (e.g., a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')2) molecule, a domain antibody, a diabody, a triabody, an affibody, a domain antibody, a SMIP, a nanobody, a Fv fragment, a Fab fragment, a F(ab')2 molecule, or a tandem scFv (taFv) fragment).

In some embodiments, the device is configured to produce an isolated population of cells from a general population of cells, wherein the isolated population of cells is enriched for one or more target populations of cells. In some embodiments, the general population of cells contains stem cells, cancer stem cells, or white blood cells, which can be separated from the general population. In some embodiments, the one or more target populations of cells are each characterized by the expression of one or more cell surface molecules (e.g., one or more of T cell receptor, CD3, CD4, CD8, CD11a, CD11b, CD11c, CD14, CD15, CD16, CD19, CD25, CD33, CD34, CD44, CD45RO, CD56, CD69, major histocompatibility complex (MHC), or a chimeric antigen receptor).

In some embodiments, the one or more target populations of cells accounts for at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) of the isolated population of cells.

In some embodiments, the one or more target populations of cells accounts for 50% or less (e.g., 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1%, 0.01%, 0.001%, 0.0001%, 0.00001%, or less) of the general population of cells.

In some embodiments, the device further includes one or more additional columns operatively connected to the outlet, wherein the one or more additional columns each including a substrate having a different binding unit. In some embodiments, the device further includes one or more three-way valves, e.g., for separating an isolated population of cells from a remainder of cells (e.g., of the general population).

In another aspect, the invention features a method for producing an isolated population of cells enriched for the target population of cells using a device of the invention.

In another aspect, the invention features a method for isolating a target population of cells by providing a suspension of cells including the target population of cells; contacting the suspension with a porous substrate to produce a population of bound cells (including the target cells) and a population of unbound cells; separating the population of unbound cells from the column; and liquefying all or a portion of the porous substrate to release the population of bound cells to isolate a target population of cells.

In some embodiments, the target cell is a T cell, a T regulatory cell, a B cell, an NK cell, a genetically engineered T cell, or a stem cell. In some embodiments, the genetically engineered T cell is a chimeric antigen receptor T cell (CAR-T cell). In some embodiments, the stem cell is an undifferentiated stem cell. In some embodiments, the stem cell is a differentiated stem cell. In some embodiments, the stem cell is a mesenchymal stem cell, a hematopoietic stem cell, an embryonic stem cell, or an induced pluripotent stem cell.

In certain embodiments of any aspect of the invention, all of the substrate liquefies upon decreased availability of a crosslinking agent. A column may be employed as a container for any purpose herein.

BRIEF DESCRIPTION OF THE DRAWINGS

FIGS. 6A-6B. Histogram plots showing the isolation efficiency and resulting purity and efficacy of CD34+Kg1A cells recovered from a mixed population sample using alginate microbeads. 6A: The total captured and released C34+Kg1A cells through the entire cell separation. 6B: The purity and recovery for C34+Kg1A cell isolation.

FIGS. 7A-7C. Representative flow cytometry data showing isolation efficiency, cell purity and viability of CD4+ T cells from a PBMC sample using alginate microbeads. 7A: Initial C4+ T cell population in PBMC sample as shown by flow cytometry. 7B: The purity, recovery, and viability of CD4+ T cells obtained by the invention. 7C: The purity, recovery, and viability of CD4+ T cells obtained by the invention.

FIGS. 8A-8C. Representative flow cytometry data showing isolation efficiency, cell purity and viability of CD4+ T cells from a population of CD3+ T cell lymphocytes using alginate microbeads. 8A: Initial CD8+ cells in CD3+ T cell population as shown by flow cytometry. 8B: Recovered CD8+ T cell purity as shown by flow cytometry. 8C: The purity, recovery, and viability of CD8+ T cells obtained by the invention.

DETAILED DESCRIPTION OF THE INVENTION

Figure 1:
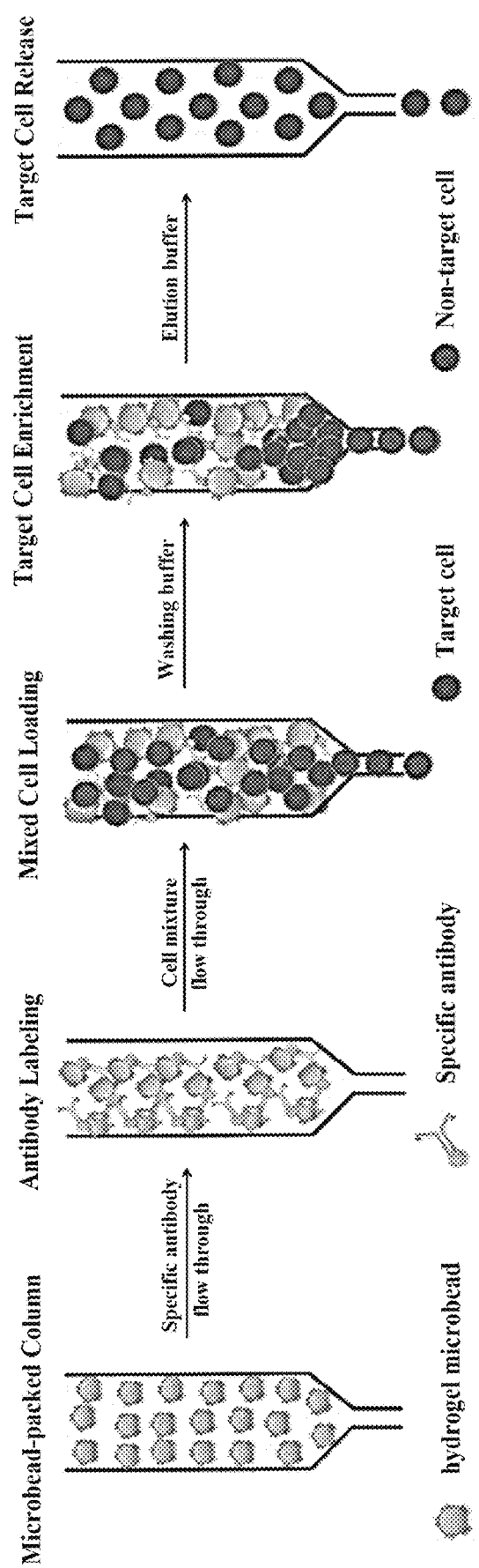
FIG. 1: A schematic workflow for the isolation of target cells by a device of the invention.

The invention provides compositions, kits, and a device including a substrate that binds a target cell population through a binding unit (e.g., an antibody or fragment thereof) specific for a desired surface molecule. Methods, including methods of using the device, are also provided by the invention.

Substrates

Substrates useful in the present invention include polymers (e.g., cross-linked polymers) that can be liquefied (e.g., dissolved) in response to exposure to biocompatible agents that reduce availability of a cross-linking agent to the polymer. Cross-linked polymers useful as part of the substrate include hydrogels, e.g., alginate hydrogels, which are solid in the presence of cations, e.g., calcium cations ($Ca^{2+}$), and liquid in the absence of these cations. Other cross-linked polymers, including hydrogels, useful as part of a substrate of the invention, are known in the art. In certain embodiments, the substrate is a porous substrate.

In certain embodiments, the substrate includes an alginate hydrogel. An alginate-based substrate may include additional components to enhance various properties, such as mechanical stiffness or liquefication threshold. A reference to alginic acid or alginate is also a reference to a salt form, e.g., sodium alginate, unless otherwise noted. An alginate-based substrate can be formed from alginic acid conjugated to a polyalkylene oxide, e.g., PEG, as generally described in WO 2012/106658. Conjugation of alginic acid to multifunctional PEG (e.g., four-armed PEG) confers greater mechanical strength compared with that achieved solely by ionic crosslinking of alginate. Polyalkylene oxides, e.g., PEG and polypropylene oxide, are known in the art. Linear or branched, e.g., 4-arm or 8-arm, polyalkylene oxides, e.g., PEG, may be employed. The polyalkylene oxide, e.g., PEG, preferably has a molecular weight between 10 kDa and 20 kDa. An exemplary ratio of polyalkylene oxide, e.g., PEG, to alginic acid is 1:2 by weight. Thus, the mechanical properties (e.g. stiffness) can be modulated by increasing the number of functional groups on each PEG molecule. PEG is useful as part of the present invention because of its superior hydrophilic properties, which prevent protein adsorption to the complex of the present invention. Adsorption of serum proteins onto the complex can result in aberrant signaling pathways in adjacent cells, such as those caused by Fc receptor engagement. The hydrophilic properties of PEG are also functional to maintain a high diffusivity within the complex interior, such that ionic chelators can rapidly access the complex interior to quickly sequester rigidity-maintaining cations. Thus, incorporation of branched PEG molecules within the hydrogel ensures a rapid dissolution of the hydrogel structure upon exposure to appropriate stimuli. Alternatively, any other biocompatible hydrophilic polymer (e.g. polyvinyl pyrrolidone, polyvinyl alcohol, and copolymers thereof) can be substituted (see, e.g., U.S. Pat. No. 7,214,245).

The hydrogel structures may be formed into any shape configured to create a substrate, e.g., for placement within a container. For example, the hydrogel can be formed into beads (e.g., spherical beads, e.g., nanoparticles, or microbeads), according to methods known in the art and described herein. Exemplary bead diameters are between 1 and 200 µm.

Hydrogel particles (e.g., alginate microbeads) can form a matrix of adjacent particles with spaces (i.e., pores) therebetween. The particles can be similar in size. Alternatively, particles can be a variety of sizes. In general, a greater the homogeneity in particle size results in a larger distance between surfaces of adjacent particles (i.e., a larger pore size), relative to particle size. This is due to the tendency of smaller particles to fill in the spaces between larger particles, occupying pore space and potentially preventing cell passage. Parameters influencing the packing of spherical particles in a space (e.g., within a column) include, e.g., the relative density of the spheres within their environment (e.g., a buffer), forces acting at the interface between one sphere and another (e.g., frictional forces or electrostatic forces), and physical agitation of the spheres. In general, attractive forces between spheres (e.g., physical or chemical adhesion, electrostatic attraction) will reduce packing and yield fewer spheres per volume, generating larger pores. Similarly, spheres having a similar density to (e.g., 1-10% greater than) their surrounding solution will generally pack less tightly and yield larger pores. The positive general relationship between sphere homogeneity and pore size can be overridden by a number of alternative methods. For example, varying the shape of all or a portion of the hydrogel structures (e.g., by including non-spherical particles) can introduce larger pores. Additionally or alternatively, different pore sizes and geometries can be introduced by using polymer of hydrogel structures of elongated fibers, tubes, or wires. Methods for synthesizing such structures, including alginate-based structures, are known in the art.

The optimal pore size can vary according to the initial cell population and/or the target cell population. For example, enrichment of a low-frequency cell population may optimally occur within a porous substrate having larger pores and, conversely, a low surface-area to volume ratio. This configuration provides enough binding opportunities for the target cells to bind to the substrate surface while permitting the majority population (i.e., the untargeted population) to freely flow through the pores. Conversely, a high relative substrate density can be used to maximize the binding area, e.g., in a scenario requiring positive selection of a large fraction of the initial cell population. A porous substrate of the present invention has pores, e.g., from about 5 µm to about 50 µm.

Additionally, other materials can be included in the substrate to provide structure and/or optimal pore sizing or architecture. For example, a dissolvable or non-dissolvable lattice or scaffold may serve to hold the substrate in place (e.g., by supporting the substrate from within a hydrogel matrix or by providing external support to hydrogel structures (e.g., microbeads)). A suitable scaffold structure will be of a sufficient configuration to permit cell passage upon liquefication of the substrate (e.g., hydrogel). For example, a scaffold may be made of fibers configured as a three-dimensional grid. Alternatively, a scaffold may have an irregular morphology (e.g., a sponge-like morphology). Methods of synthesizing such scaffolds are known in the art for applications such as three-dimensional cell culture (e.g., tissue engineering), and include particle leaching (e.g., salt leaching), emulsion freeze-drying, electrospinning, and 3D-printing. Suitable materials for a lattice or scaffold can be biocompatible, e.g., biocompatible polymers. Biocompatible polymers are well known in the art for construction of scaffolds having various, defined pore sizes and include, e.g., bio-degradable aliphatic polyesters such as polylactic acid (PLA), polyglycolic acid (PGA), poly(D,L-lactide-co-glycolide) (PLGA), poly(caprolactone), diol/diacid aliphatic polyester, polyester-amide/polyester-urethane, poly(valerolactone), poly(hydroxyl butyrate) and poly(hydroxyl valerate) or one or more natural polymers selected from a group consisting of chitosan, chitin, collagen, gelatin and hyaluronic acid. Magnetic beads may also be used as a non-dissolvable lattice for hydrogels.

Figure 5:
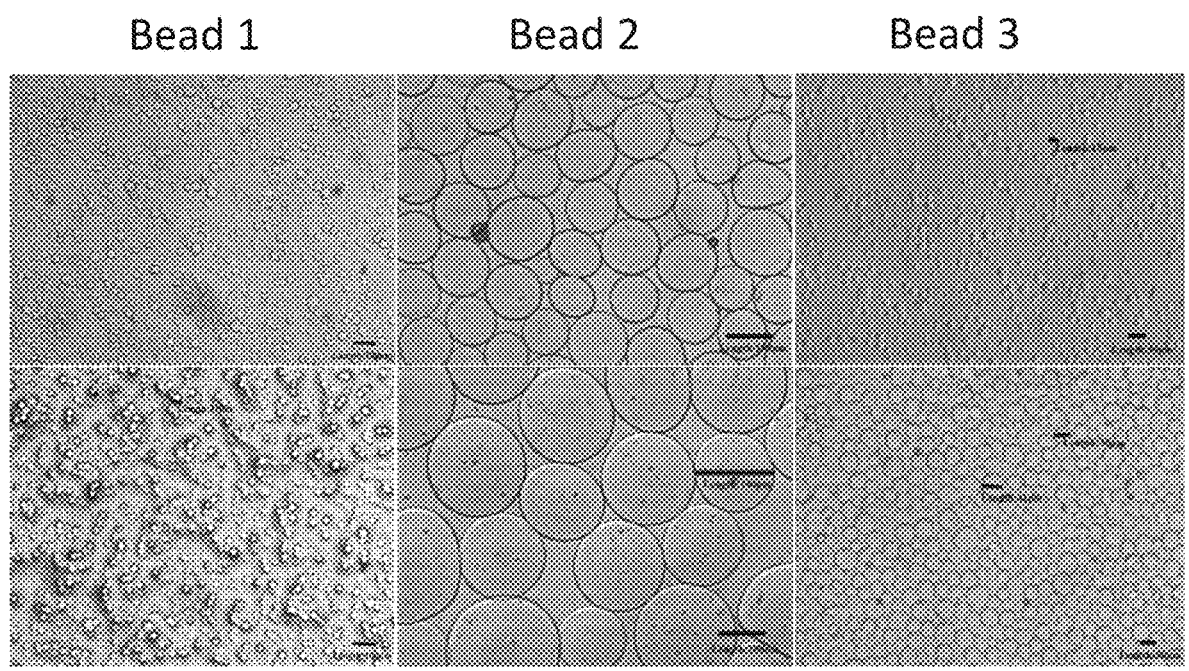
FIG. 5. Representative brightfield microscopy images of different types and sizes of alginate microbeads.

The substrate can be in the form of a plurality of hydrogel microbeads of a polycation cross-linked alginate-PEG copolymer hydrogel (FIG. 5). These microbeads can have a diameter between 1-1000 µm (e.g., 2-500 µm, 3-200 µm, 4-100 µm, or 5-20 µm). The microbeads can have a polydispersity index (PDI) between 1-2. The microbeads have surfaces that are functionalized with binding units or with moieties capable of binding to binding units.

The substrate of the invention may be in dried form, e.g., by lyophilization, and be rehydrated prior to or during use.

Devices

A device of the invention includes a container and a porous substrate within the container. The porous substrate can either be a plurality of structures (e.g., particles, e.g., microbeads, packed within the container), a monolithic (i.e., integrated) structure, a coating or surface layer on an underlying scaffold or core, or any combination thereof. Alternatively, the porous substrate can be contained within a packed bed. Porous substrates of the invention are degradable by, e.g., addition of a biocompatible solution suitable to liquefy the porous substrate. Binding units configured to selectively bind surface molecules of target cells within the pores of the substrate are attached to the porous substrate. The binding units can be antibodies or an antigen-binding fragment of an antibody. Binding units can form affinity bonds with cell surface molecules to immobilize target cells against shear forces within the pores of the substrate in the container (e.g., upon washing unbound cells from the container). FIG. 1 shows a schematic workflow for the isolation of target cells by a device of the invention. The invention also features devices including multiple containers connected, e.g., in series or in parallel.

Containers used to hold the porous substrate of the invention can be of varying types. Suitable containers include columns or troughs of an appropriate volume. The optimal volume of the container will depend on the number of target cells to be isolated. For small scale cell processing, the volume can be about 15 mL or less. Other volumes, e.g., for large-scale processing, can be 100 mL or greater.

The device will include a component that retains the porous substrate but allows cells to pass. Such a component can be a strainer, e.g., a mesh or a sieve. The openings in the strainer, which may or may not be uniform, are chosen based on the size of cells being targeted as well as the nature of the porous substrate. For example, the openings can be between 1-1000 µm, e.g., 1-30 µm, 10-40 µm, 20-30 µm, 5-50 µm, 20-80 µm, 1-100 µm, 200-500 µm, or 500-1000 µm. For example, openings between 1 µm to 100 µm can be used to isolate and purify the single or multiple target cells with improved recoveries directly from complex environments such as PBMC or whole blood at a small scale or a large scale. Larger mesh sizes between 200 µm to 500 µm with improved ventilation to avoid clogging can be used for the physical disruption of rough tissue like muscle, fat, skin, lung or similar to gain primary cells, making them ideal for stem cell, cardiomyocyte, neurological and skeletal tissue applications while enabling faster separation of large volumes of cellular material and improved recoveries.

Devices of the invention may further include two or more containers attached in series. In this configuration, the outlet of a first container is operatively connected to an inlet of a subsequent container, permitting passage of cells from the first column to one or more subsequent containers. Each container can have the same porous substrate or a different porous substrate, and the same binding unit or a different binding unit. Separating the containers (e.g., at the interface of the first container's outlet and the subsequent inlet of the second container) can be a valve (e.g. a two-way valve). A valve can be configured to dictate the direction of flow of cells from a first container into one or more subsequent containers or, alternatively, out of the series of containers into a capture reservoir, for example.

The valve mechanism can include two successive T-shaped three-port valves. The first valve contains two passageways which allow fluid or cells to flow freely into either the second valve or a third passageway, e.g., containing a filter. This filter can be used during the addition of a chelator by retaining the target cell population while allowing the chelator solution to flow into the second valve and out of the system, preventing subsequent containers from coming into contact with the chelator. The second valve contains three passageways to allow a solution (e.g., a wash solution or chelator solution) to either exit the device (e.g., for disposal or recovery) or flow into subsequent containers (e.g., for wash or elution of multiple columns in series). The valves can either be controlled manually or by actuators (e.g., by electric motor or solenoid).

Any device of the present invention can be scaled up according to methods known in the art to generate large quantities of functional cells, e.g., for clinical applications, such as adoptive cell transfer.

Kits

The invention also provides kits including a substrate as described herein and a strainer, e.g., a mesh or sieve. The strainer is sized to allow cells to pass but not the substrate, e.g., having openings between 1-1000 µm, e.g., 1-30 µm, 10-40 µm, 20-30 µm, 5-50 µm, 20-80 µm, 1-100 µm, 200-500 µm, or 500-1000 µm, as described above. The strainer may be housed in a container capable of containing the substrate and a population of cells. Alternatively, the strainer may be a separate component that can be added to such a container.

The substrate may include binding units or be designed to be functionalized by a binding unit. An exemplary substrate is a plurality of hydrogel microbeads of a polycation cross-linked alginate-PEG co-polymer hydrogel. These microbeads can have a diameter between 1-1000 µm (e.g., 2-500 µm, 3-200 µm, 4-100 µm, or 5-20 µm). The microbeads can have a polydispersity index (PDI) between 1-2.

Binding Units

The invention features solid substrates functionalized with binding units (e.g., by surface functionalization). A binding unit is any molecule having a greater binding affinity for a target molecule than a non-target molecule. The binding units may be any small or large molecular structure which provides the desired binding interactions with the cell surface molecules (e.g., proteins, carbohydrates, or combinations thereof) on the target cell.

Binding units include antibodies and antigen binding fragments and variants thereof, which are known in the art. An antibody variant of the invention includes a monoclonal antibody, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv') 2) molecule, a domain antibody, a diabody, a triabody, an affibody, a domain antibody, a SMIP, a nanobody, a Fv fragment, a Fab fragment, a F(ab') 2 molecule, or a tandem scFv (taFv) fragment. Antibodies, including both polyclonal and monoclonal antibodies, may be raised against a target cell surface molecule using conventional techniques, as described in Harlow and Lane, eds., Antibodies: A Laboratory Manual, Cold Spring Harbor Laboratory, Cold Spring Harbor, N.Y. (1988). A binding unit of the invention can also be a nucleic acid (e.g., an aptamer) that has a high affinity for a specific epitope.

Binding units also include adhesion molecules, or mimics thereof, present on another cell, a pathogen, or an extracellular matrix molecule, where the adhesion molecule is a natural binding partner to cell surface molecule on a target cell. Such adhesion molecules are usually proteins or glycoproteins, and the binding units of the present invention are can be fragments of such adhesion proteins which retain the natural binding activity. Such fragments typically comprise 50 or fewer amino acids, fewer than 25 amino acids, or fewer 10 amino acids.

Additional suitable binding units may be molecules present in the extracellular matrix, particularly in matrix proteins, such as fibronectin, collagen, laminin, proteoglycans, elastins, hyaluronic acids, fibrinogens, vitronectins, osteoportins, and fragments thereof (e.g., RGD domains).

A binding unit may bind to another binding unit, e.g., an antibody or antigen-binding fragment thereof, bound to the target cells. For example, the binding unit may be avidin or streptavidin, and it may bind to a target cell that has been labeled with biotin, e.g., via biotinylated antibodies. Other such binding units include protein A, protein G, and anti-species antibodies (e.g., goat anti-rabbit antibodies) that bind to antibodies bound to a target cell.

A binding unit of the invention may be a multimeric binding unit. Multimeric binding units are known in the art and are useful for binding low-affinity ligands. For example, major histocompatibility complex (MHC) multimers (e.g., dimers, tetramers, or dextramers) are widely used to bind T-cell receptors (TCRs) in an antigen-specific capacity, because the affinity of MHC molecules for TCRs is several orders of magnitude lower than antibody-antigen affinities. By tethering two or more binding units in close proximity (e.g., through avidin multimerization or by a multi-arm PEG chain) multimeric binding units bind targets at a high density and with high avidity, resulting in a lower rate of dissociation. Other approaches to multimerizing various binding units are known in the art.

It will be appreciated that the binding unit may include a variety of other molecular structures, including lectins, nucleic acids, and other receptor ligands, and fragments thereof. Once a desired target molecule is known, it will be possible to prepare or synthesize other molecules which are capable of binding the target with the requisite affinity or avidity (see, e.g., methods of antibody synthesis described above).

The binding unit of the present invention can be conjugated to the substrate. This conjugation can occur through a covalent reaction or a non-covalent reaction by known methods. For example, biotinylated antibodies and other molecules are well-characterized for binding to avidin or variations thereof (e.g., streptavidin or neutravidin). A substrate can be functionalized with avidin according to methods known in the art. Specifically, an avidin-biotin (e.g., streptavidin-biotin) binding system can be used to attach various binding units to one another or onto a substrate. Maleimide-activated streptavidin can be attached via reduce thiol-groups present on alginate microbeads. Avidin-functionalized substrates provide a modular foundation for a user to customize the device according to the phenotype of his or her desired target cell population, e.g., by adding a biotinylated antibody of his or her choice immediately prior to use. Alternatively, a substrate may be conjugated with biotin, to which an avidinylated binding unit may be subsequently attached.

Hydrogels, such as alginate hydrogels, can be conjugated with biotin, avidin (e.g., streptavidin), or directly conjugated with a binding unit (e.g., antibody or antigen binding fragment thereof) according to known methods. A hydrogel can be solidified prior to conjugation to maximize efficiency of binding units due to restriction of conjugation to the surface of the hydrogel.

Alginic acid also naturally possesses multiple carboxyl groups that provide convenient groups for conjugation to polyalkylene oxide, e.g., polyethylene glycol (PEG), and/or binding units. The polyalkylene oxide, e.g., PEG, and binding unit will naturally possess or be modified to possess an appropriate group to conjugate to a carboxyl group. Suitable groups include amine groups, which are often found in binding units that include amino acids or can be introduced into binding units and polyalkylene oxides, e.g., PEG. For example, amine-terminated polyalkylene oxide, e.g., PEG, can be employed. In other cases, a linker may be use to conjugate appropriate groups on the polyalkylene oxide, e.g., PEG, or binding unit to carboxyl groups on the alginic acid. In the hydrogel, a single polyalkylene oxide, e.g., PEG, may be conjugated to one or more alginic acid molecules. When a polyalkylene oxide binds to more than one alginic acid, the number of such crosslinks in the composition may or may not be sufficient to form a gel. The binding unit can bind to either the alginic acid directly or to a polyalkylene oxide, e.g., PEG, bound to alginic acid.

Additionally or alternatively, direct covalent attachment between available binding functionalities on the substrate and on the binding unit can be achieved by conventional techniques relying on activation of either or both of the functionalities. Covalent attachment between the binding unit and the substrate can be achieved using a bifunctional compound having a reactive group at one end which is capable of binding to the binding unit and a second reactive group at the other end which is capable of binding to the substrate. Alternatively, a linking region may be synthesized together with the binding unit which may then be directly coupled to the porous substrate. Reagents useful for covalent attachment include, e.g., carbodiimides, e.g., water soluble carbodiimides. Other reagents and techniques useful for conjugating a binding unit to a porous substrate are known in the art can be found, e.g., in Hermanson (Bioconjugate Techniques, Academic Press, San Diego, 2010). Numerous other conjugation chemistries are known in the art.

Methods of Use

The invention features for separating one or more populations of cells from each other or a general population by affinity chromatography. Cell selection is based largely on the difference in capture force between specific and nonspecific binding. The cells with specific binding (i.e., target cells) will be retained while the cells with non-specific or lack of binding can be removed for discarding, use, or further separation. A "target cell," as used herein, refers to a cell that is targeted by a binding unit of the invention and intended to bind to the porous substrate. Target cells may be recovered by liquefying the substrate. Non-target cells are cells that are not intended to bind to a binding unit. This selection can either be a positive selection process (i.e., retaining target cells on the porous substrate) or a negative selection process (i.e., retaining non-target cells that pass through the porous substrate). The invention features methods of positive selection that produce an enrichment of target cells that do not have residual affinity tags (e.g., magnetic beads) on their surface. A negative selection process may be favorable if, e.g., a desired cell surface molecule profile is poorly characterized or unknown, or if the undesired cell population ubiquitously expresses a surface molecule that simplifies its targetability. In one example, the invention provides a method for separating a target population of cells by providing a suspension of cells (e.g., a general population of cells) including the target population of cells; contacting the suspension with a substrate to produce a population of bound cells (e.g., including the target cells) and a population of unbound cells; and removing the population of unbound cells. The method may also include liquefying all or a portion of the substrate to release the population of bound cells to isolate a target population of cells. Prior to the binding step, the cells may be contacted with a binding unit, e.g., an antibody, not attached to any substrate, where this binding unit is subsequently bound to the substrate as described herein.

Cells that can be targeted for enrichment, isolation, purification, or separation by the invention include any cell that can be identified by one or more surface molecules (e.g., proteins, carbohydrates, or combinations thereof). Target cells can be mammalian cells (e.g., mouse, rat, non-human primate, or human cells) or non-mammalian. Cells can be isolated as a mixed population from one or more tissues, e.g., as part of a blood draw, biopsy, or necropsy. Unwanted cells within a tissue, such as red blood cells or stromal cells, can be removed (e.g., by lysis or adhesion separation) according to methods known in the art. Cells can be freshly isolated from storage, e.g., thawed from a frozen suspension. Cells can be primary cells or immortalized cells (i.e., from cell lines).

Surface molecules of target cells are largely known in the art. Any surface molecule that can be detected by conventional assays that detect surface molecules, e.g., immunoassays, such as enzyme-linked immunosorbent assay (ELISA), western blot, immunohistochemistry, immunofluorescence, or flow cytometry) can be used as a target. Specific surface markers that can be targeted include CD3, CD4, CD8, CD11a, CD11 b, CD11c, CD14, CD15, CD16, CD19, CD25, CD33, CD34, CD44, CD45RO, CD56, CD69, and major histocompatibility complex (MHC) (e.g., MHC-I, MHC-II, human leukocyte antigen class I, human leukocyte antigen class II, or any gene or pseudogene product thereof).

Cell types that have characteristic surface molecule expression enabling their affinity-mediated selection (e.g., through positive selection, negative selection, or both) include, e.g., $CD3^+$ T cells, $CD4^+$ T cells, $CD4^+$ naïve T cells, $CD4^+CD25^+$ regulatory T cells (T regulatory cells, or Tregs), $CD4^+$ memory T cells, $CD8^+$ T cells, $CD19^+$ B cells, $CD56^+$ NK cells, $CD14^+CD16^-$ monocytes, $CD14^+CD16^+$ monocytes, pan dendritic cells, eosinophils, basophils, neutrophils, $CD34^+$ hematopoetic progenitors, mesenchymal progenitors, and skin and intestinal stem cells.

Enriched cells (e.g., target cells resulting from a positive selection process of the invention or non-target cells resulting from a negative selection of the invention) can retain their functionality and viability after isolation or enrichment. Enriched cells can be from 80%-100% viable (e.g., at least 80%, 85%, 90%, 91%, 92%, 93%, 94%, 95%, 96%, 97%, 98%, 99%, or 100% viable). Enriched cells can also retain proliferative capacity (e.g., upon TCR engagement or other stimulation, e.g., of at least 80%, 85%, 90%, 91%, 92%, 93%, 94%, 95%, 96%, 97%, 98%, 99%, or 100% proliferative capacity of control cells).

Target cells may be contacted with the substrate by any suitable method. The contacting may or may not occur in the container in which bound cells are separated from unbound cells. For example, cells and a substrate may be contacted in a first container to allow for binding. This mixture can then be transferred to a second container having a strainer that retains the substrate (and bound cells) while allowing unbound cells to pass. In other embodiments, the cells and substrate, e.g., a porous, substrate are contacted in the container in which separation will occur. For example, contacting may occur by inserting the suspension of cells (e.g., a general population of cells, e.g., any cells described herein by, e.g., pipetting, pumping, or injecting the suspension of cells, e.g., automatically or manually) into the inlet of a container.

A general population of cells can be prepared in a suitable buffer (e.g., a buffer containing serum) prior to contacting the substrate. Target cells will begin to bind to the substrate through the binding unit according to various parameters including, e.g., temperature, binding affinity between the binding unit and the target surface molecule, and density of the binding unit on the substrate. This step can be of a duration from a one second to one or more days (e.g., 1 second, 30 seconds, 1 minute, 5 minutes, 10 minutes, 15 minutes, 20 minutes, 25 minutes, 30 minutes, 1 hour, 2 hours, 4 hours, 6 hours, 8 hours, 12 hours, 18 hours, 24 hours, or more) at any suitable temperature (e.g., 4° C., 25° C., or 37° C.). The pH of this binding reaction can be at about 7.4 or at any other physiologically suitable pH that facilitates a specific binding reaction. The container used for contacting can be capped or covered during this reaction to maintain temperature or to prevent evaporation or contamination.

Additional agents, such as proteins (e.g., serum proteins, e.g., albumin) can be included in the binding reaction step, e.g., to limit non-specific binding. Such proteins can be added before addition of the cells, after addition of the cells, or simultaneously with addition of the cells (e.g., as a component of the cell suspension buffer). These serum proteins can be of the same of a different species of the cells.

After all or a portion of the target cells are bound to the substrate, the unbound cells can be removed (e.g., washed) away from the target cells, according to methods known in the art. Specifically, a suitable buffer (e.g., HEPES, Hanks buffered saline, HBSS, MOPS, and MES supplemented with calcium) can be used. Optionally, one or more additional agents can be included in the wash buffer (e.g., a serum protein of the same or greater concentration to any other serum present in any solution of the invention) to enhance removal of unbound cells. Unbound cells that are eluted can be collected for use or transferred to an additional container, e.g., for multiparametric enrichment, as described above.

Methods of the invention may include preparing a porous substrate within a container according to methods known in the art. A substrate, e.g., a porous substrate, can be synthesized according to methods described herein and prepared within a container in various ways. A substrate can be pre-packed into a container, or it can be prepared immediately prior to use. Pre-packed substrates can be dried (e.g., lyophilized) for long term storage. Alternatively, pre-packaged substrates can be kept hydrated (e.g., to avoid denaturing sensitive binding domains of the binding units). A pre-packaged substrate can be kept at, e.g., 4° C., for long term storage (e.g., for one or more weeks or months, depending on the stability of the binding unit and buffer conditions). A binding unit can be conjugated to the substrate before or after loading the substrate into the container. For example, a substrate can be stored in conditions allowing conjugation to the binding unit immediately prior use.

Figure 2:
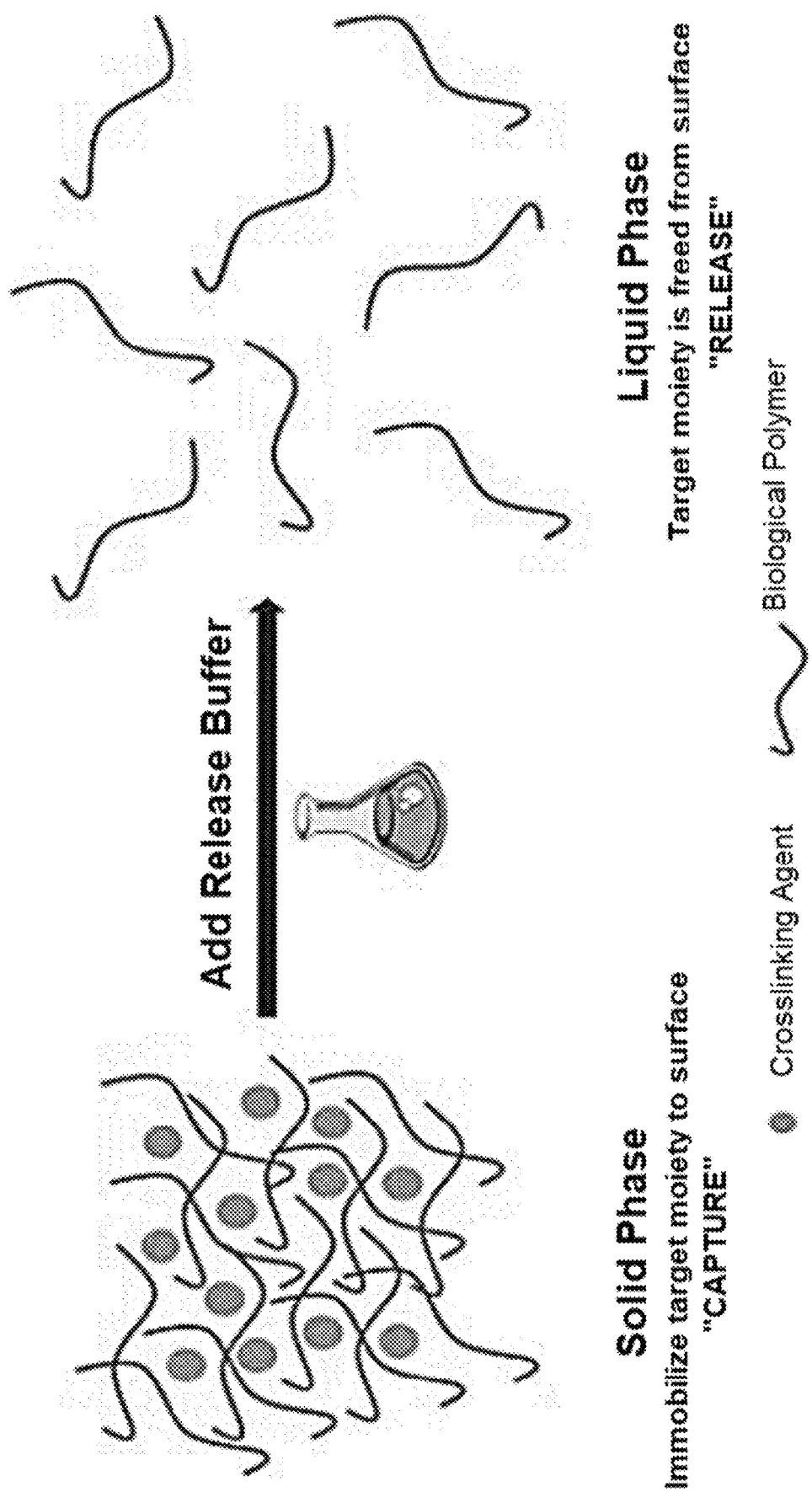
FIG. 2: A diagram illustrating the change in molecular structure of a polymer matrix in response to a release buffer.

A substrate (e.g., a cross-linked hydrogel) can be liquefied, in whole or in part, with low-to-moderate concentrations of biocompatible solutions. FIG. 2 is a diagram illustrating the change in molecular structure of a polymer matrix in response to a release buffer. A hydrogel can be maintained as a solid by noncovalent crosslinking of the alginic acid with a cation, e.g., $Li^+$, $Mg^{2+}$, $Ca^{2+}$, $Sr^{2+}$, $Ba^{2+}$, $Zn^{2+}$, $Cu^{2+}$, or $Al^{3+}$. A preferred cation is $Ca^{2+}$. Gelation of hydrogels of the invention may be reserved by contact with a chelator for the cation, e.g., EDTA, EGTA, sodium citrate, BAPTA, crown ether, cryptand, phenanthroline sulfonate, dipyridyl sulfonate, dioxane, DME, diglyme, or triglyme. The chelator can be a bioinert molecule such as EDTA, which is well-known not to interfere with cell growth and proliferation pathways at concentrations relevant for complex dissolution. EDTA is a well-characterized calcium chelator of use in the present invention. EDTA can be used at 2 mM in the form of a physiologically insert buffer that preferably also contains 137 mM NaCl, 2.7 mM KCl, 25 mM Hepes and 0.75 mM $Na_2H_2PO_4.2H_2O$.

Liquefying the substrate in a manner consistent with the composition of the substrate can be used to remove the target cells from a container. The invention includes a method of liquefying an alginate hydrogel substrate (e.g., of alginate beads, e.g., microbeads) by sequestering a crosslinking agent to a necessary degree for the alginate matrix to de-crosslink. A buffer comprising a chelator at a suitable concentration (e.g., from 0.01 mM to 1000 mM, e.g., 0.1 mM, 0.5 mM, 1.0 mM, 2.0 mM, 3.0 mM, 4.0 mM, 5.0 mM, 10 mM, 50 mM, 100 mM, 500 mM, or 1000 mM, depending on other parameters such as incubation time and temperature) can be added to a container to liquefy all or a portion of the alginate substrate. In certain embodiments, the substrate and bound cells are removed from the container prior to liquefaction.

It is sometimes desirable to isolate a population of cells characterized by the expression of two or more molecules. The invention provides methods of isolating such cells (e.g., double-positive or triple-positive cells). Isolation of a double positive cell population can be achieved by contacting a mixed cell population with multiple sets of substrates. For example, this goal can be accomplished by passing a mixed cell population through a series of containers, each container containing a unique binding unit. It will be understood that multi-parametric enrichment may also occur in a single container in which the substrate is removed and replaced after each separation. Furthermore, the same type of substrate, e.g., where the binding unit is streptavidin, if the cells are contacted with different binding units, e.g., biotinylated antibodies, separately from the substrate.

Figure 3:
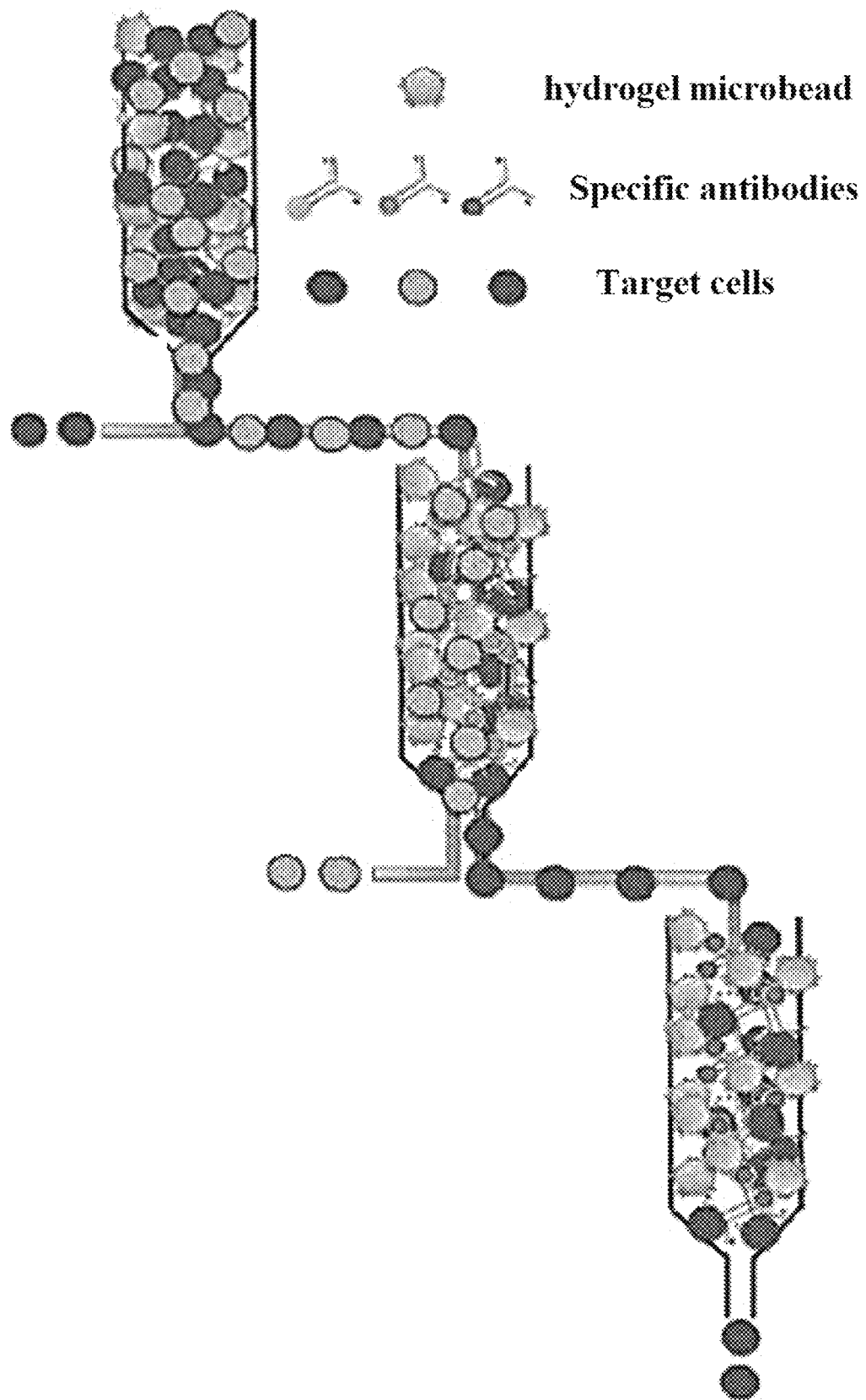
FIG. 3: A schematic diagram showing three microbead-packed containers connected in series for enrichment of double or triple-positive cells.

FIG. 3 is a schematic diagram showing three microbead-containing containers, e.g., columns, connected in series. This configuration could be used to recover a cell population enriched for up to three surface molecules. Each of the three surface molecules would be targeted by a different binding unit within each of the three containers. In the first container, a binding unit associated with the first microbead substrate would bind a population of cells expressing the first surface molecule. Unbound cells could be washed through the container and removed from the series of containers by passing through an exit port, controlled by a three-way valve at the outlet of the container, as described above. The valve could then be switched in preparation for guidance of the target cell population into the second container, according to methods described above. The cells of the first container can then be released from the microbeads and eluted into the second container containing microbeads coated with a binding unit to a second surface molecule of interest. Cells binding to the microbeads of the second container will generally express both the first and the second surface marker of interest (i.e., double positive). Elution can be repeated a third time, into a third container, to recover a triple-positive population of cells. Unbound cells at any step of the process can be further enriched by passing through another container to recover various subtypes of cells.

For example, regulatory T cells (Tregs), which express CD4 and CD25, can be isolated by using anti-CD4 antibodies as a binding unit on a first substrate to immobilize $CD4^+$ cells of, e.g., a blood sample, and remove the $CD4^-$ cells. The hydrogel can be liquefied to release the $CD4^+$ cells, and these cells can be transferred (e.g., automatically or manually) into contact with another substrate having anti-CD25 antibodies as a binding unit. $CD4^+CD25^-$ cells will not bind to the binding unit of this second substrate and can be washed away for discarding or used as, e.g., naïve $CD4^+$ cells (i.e., Th0 cells), leaving the $CD4^+CD25^+$ cells behind to be recovered for use as Tregs.

The method described above can similarly be used to isolate two or more (e.g., 2, 3, 4, 5, 6, 7, 8, 9, 10, or more) cell types from a single sample. Cell populations having any permutation of detectable surface molecules can be similarly enriched or isolated for use, because cells isolated by positive selection of the invention retain viability and function due to the lack of residual affinity tags.

Multiple cell types can be targeted in a single container by using two or more binding units within the device (e.g., within the same column). Similarly, slight variations in binding units may improve target cell binding by, e.g., binding to multiple epitopes of the same surface molecule. Polyclonal antibodies, e.g., are suitable for use by this approach.

The method described above can similarly be used to pre-select a specific cell population for further cell sorting and binning methods, such as fluorescence-activated cell sorting (FACS) or other similar flow cytometric methods.

Production of Hydrogels

In general, alginate particle formation is based on two methods. Complex formation can occur in an aqueous solution forming alginate nanoaggregates or on the interface of an oil droplet, forming alginate nanoparticles. A cross-linker, such as calcium from calcium chloride, can be used for the complexation of alginate. Alternatively, alginate-in-oil emulsification can be used to formulate alginate beads (e.g., nanoparticles or microbeads). This technique can be coupled with external or internal gelation of the alginate emulsion droplet, forming alginate nanoparticles. The majority of these methods are based on an external gelation method, where alginate beads are usually produced by drop-wise extrusion of sodium alginate solution into calcium chloride solution. Alginate can also interact with cationic polymers, such as chitosan, and form a polyelectrolyte complex. Thus, alginate particles can also be obtained by dripping an alginate solution in a bath containing a cationic polymer. Typically an alginate solution is extruded through a needle to form alginate droplets and alginate particles size depends on the size of the initial extruded droplet. Small particles have a higher mechanical strength and a larger specific surface area. Air atomization can be used for the formation of alginate particles, when coupled with external gelation, and yields microbeads of 5-200 µm in diameter. Modified emulsification or internal gelation methods, alternative to extrusion/external gelation, are known in the art. For example, emulsification can be performed at ambient temperature to produce alginate beads without specialized equipment.

In certain embodiments, the hydrogel is produced using a spray apparatus (e.g., an apparatus including an atomizer). In general, a polymer solution (e.g., an aqueous solution of alginic acid-PEG) can be injected into an atomizer simultaneously with a compressed gas (e.g., nitrogen) to atomize the polymer solution, projecting a spray of droplets. This spray can be directed into a receiving liquid configured to harden the droplets into beads. In cases in which the polymer solution includes alginic acid-PEG, the receiving solution may include a cation (e.g., a polycation, e.g., $Ca^{2+}$), and, upon contact between the alginic acid-PEG droplets and the cationic receiving solution, alginic acid molecules within the droplets become crosslinked by the cation (e.g., the polycation, e.g., $Ca^{2+}$), and hydrogel beads are formed. Additional components may be included as part of the receiving solution. For example, the receiving solution may include isopropyl alcohol, e.g., to further harden the beads during and/or after cationic crosslinking. Additionally or alternatively, the receiving solution may include other stabilizers and/or surfactants known in the art, as required.

Desired bead size can be achieved by tuning various parameters of the methods of the present invention. Generally, bead size (and, e.g., resulting hydrogel complex size) is related to the size of the droplets formed in the atomized spray (e.g., bead size is proportional to (e.g., directly proportional to) or slightly less than the size of the droplets formed in the atomized spray). Absent external variables, droplet size (and resulting bead or complex size) tends to decrease with (i) increasing gas pressure or gas flow rate through the atomizer, (ii) decreasing volumetric percentage of liquid flowed through the atomizer, (iii) decreasing viscosity of the polymer solution, and (iv) increasing spray angle.

In some cases, hydrogel bead s are formed using an atomizer that sprays at a volumetric percentage of liquid from 30% to 90% by volume. At these volume fractions, the size of resulting hydrogel beads will depend on other factors discussed above, but can range from 1 to 100 μm in mean diameter.

The volumetric percentage of liquid (e.g., copolymer solution) to gas (e.g., nitrogen) is a function of the relative flow rate through the atomizer of the liquid relative to the gas. Accordingly, increasing the flow rate of gas relative to liquid through an atomizer will tend to result in smaller droplet size (and, e.g., smaller bead size). Gas flow rates can be controlled by pressurized reservoirs. In many cases, a gas source is a pressurized tank, and the rate of gas flow into the atomizer is controlled by a pressure control and/or regulator valve. Alternatively, gas may be flowed through an atomizer by other means, such as pumps (e.g., pressure-controlled pumps). Any gas reservoir providing a constant flow into the atomizer is suitable for use as part of the present invention.

Similarly, a liquid (e.g., a polymer solution) can be flowed through the atomizer using a pressurized reservoir, such as a syringe pump (e.g., a syringe pump set to a constant flow rate). Alternatively, other pump formats can be used to drive liquid flow (e.g., polymer solution flow), such as peristaltic pumps. Systems such as peristaltic pumps may provide the benefit of scalability, by enabling large volumes of liquid processing over extended durations. However, any liquid reservoir providing a constant flow into the atomizer is suitable for use as part of the invention.

The atomizer can be configured such that liquid flow and gas flow can be controlled independently. Such atomizers include external mix atomizers, in which the gas and liquid streams exit the atomizer nozzle at separate points. External mix atomizers enable an average atomized droplet size (and, e.g., the resulting average bead size) to be increased or decreased, for example, by decreasing or increasing, respectively, the gas flow rate, while holding the liquid flow rate constant. External mix atomizers may also more effectively atomize viscous liquids.

Alternatively, an internal mix atomizer may be used. Internal mix atomizers introduce the gas to the liquid within the nozzle and, in some instances, enable production of smaller droplets.

Further control over the volumetric percentage of liquid (e.g., polymer solution) to gas (e.g., nitrogen) can be maintained, for example, by attaching the liquid reservoir (e.g., syringe pump) to the atomizer using a ball valve to permit liquid flow upon liquid pressurization, thereby preventing variability in volumetric percentage at the start and finish of the atomization process.

Polymer solutions can be viscous (e.g., of a greater viscosity than water, i.e., greater than 1 centipoise (cP)). Viscosity will depend on the concentration of the polymer (e.g., alginic acid-PEG copolymer). A liquid's viscosity is positively correlated with atomized droplet size (and, e.g., resulting bead size). The relationship between an atomized droplet size of a viscous solution and a corresponding atomized droplet of water can be estimated as:

$$D_f \approx D_x V_f^{0.2}$$

where $D_f$=the droplet size of the viscous liquid, $D_w$=the droplet size of water, and $V_f$=the viscosity (cP) of the viscous liquid.

It will be understood that, in the case of a non-Newtonian fluid (e.g., a non-Newtonian copolymer solution, e.g., a non-Newtonian copolymer solution containing alginic acid-PEG), viscosity varies with shear rate. For example, a copolymer solution containing alginic acid and/or PEG may exhibit shear thinning behavior, such that its viscosity decreases with increasing shear rate. In some cases, the apparent viscosity of a copolymer solution decreases by greater than 50% upon exposure of shear forces with an atomizer. Thus, in evaluating the effect of viscosity on hydrogel particle size, a copolymer solution's apparent viscosity within the atomizer orifice should be considered. Factors that influence the apparent viscosity of a non-Newtonian fluid under a given shear rate (e.g., within an atomizer) are known in the art and can be calculated and/or empirically tested by known methods.

The spray angle of an atomizer is yet another parameter that influences droplet size. In general, a wider the spray angle correlates with a smaller resulting droplet size.

After hydrogel bead synthesis, the beads can be filtered using standard methods (e.g., sterile filtration methods, e.g., using a 140 μm nylon filter). Bead suspensions can otherwise by concentrated or purified, e.g., by standard centrifugation/resuspension methods.

Additionally or alternatively, hydrogel beads can be synthesized using methods currently known in the art. For example, hydrogel complexes can be formulated as micro beads by conventional microemulsion processes. Methods for synthesizing alginate beads for various applications are known in the art (see, for example, Hatch, et al., *Langmuir* 27 (2011): 4257-4264 and Sosnik, *ISRN Pharmaceutics* (2014):1-17).

Binding moiety conjugation (e.g., antibody conjugation) can be carried out using standard conjugation techniques including malieimide/thiol and EDC/NHS linking. Other useful conjugation methods are described in Hermanson et al., (2013) Bioconjugate Techniques: Academic Press. In some cases, binding moiety conjugation occurs immediately following particle formation, e.g., as described above. Alternatively, particles are stored (e.g., as frozen suspensions or lyophilized powders) prior to conjugation with binding moieties, and binding moiety conjugation is performed prior to cell treatment (e.g., immediately prior to cell treatment, with or without further purification, e.g., filtration and/or centrifugation/resuspension).

EXAMPLES

Example 1

A schematic workflow for the isolation of target cells is provided in FIG. 1. A column is packed with hydrogel (e.g., alginate) microbeads, which is conjugated to antibodies specific for a target cell surface molecule. In this example, the microbeads are loaded into the column prior to conjugation with the antibody. Alternatively, antibody-conjugated microbeads can be directly loaded into the column. After the antibody-conjugated microbeads are prepared in the column, a mixed cell population (e.g., peripheral blood mononuclear cells (PBMCs), cord blood, bone marrow, mixed lymphocytes, tumor cells) is loaded into the column. The mixed cell population is incubated in the column at 4° C. or 37° C. for a period of time (e.g., 5-30 minutes) to allow the antibodies to bind to their cognate cell surface molecules on the target cells. After binding takes place, a wash buffer is added to the column to wash unbound cells from the column, e.g., through the exit port. One or more wash steps is performed to remove as many unbound cells as possible. Next, a liquefication buffer is added to dissolve the hydrogel microbeads. The liquefication buffer can be any biocompatible solution configured to dissolve the hydrogel microbeads by changing the ionic concentration within the column. Specifically, the elution buffer can be a buffered saline (e.g., PBS) containing a suitable concentration of EDTA to chelate calcium ions, thereby de-crosslinking the alginate matrices of the microbeads.

Example 2

The separation of single or multiple target cells from complex environments such as PBMC and whole blood is described with the following the following sequence of steps: 1. Label cells with target-specific antibody; 2. Bind alginate hydrogel microbeads to the antibody-labeled cells; 3. Complexes of the microbeads and cells are added to a' device format such as columns, strainers, or centrifugal devices to perform cell separation steps, e.g. sample loading, washing, and elution.
Specific Antibody Labelling with Target Cells.

Starting populations of, e.g., 1, 5, or 10 million PBMC or other cell populations, can be incubated with specific antibodies for target cell selection at room temperature or 4° C.
Alginate Hydrogel Microbeads Bound with Antibody-Cells.

Figure 4A:
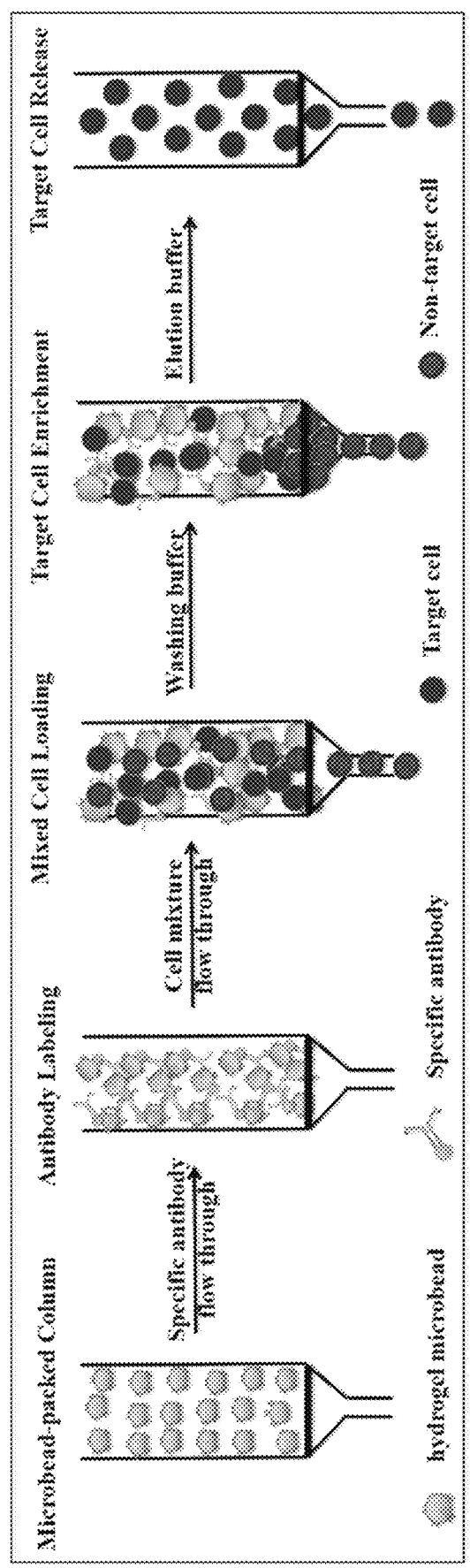
FIGS. 4A-4B. Schematic diagrams showing on-column (FIG. 4A) and off-column (FIG. 4B) separation methods.

After unbound antibody removal, 50 or 100 μL streptavidin-conjugated alginate hydrogel microbeads can be mixed with antibody-labelled cells in 1× Cell Separation Buffer followed by shaking of the mixture at room temperature for 1 h. The Cell Separation Buffer is a pH 7.4 buffered salt solution containing a chelating agent. The solution contains 25 mM HEPES, 137 mM NaCl, 2.7 mM KCl, 10 mM $CaCl_2$), and 0.5% w/v bovine serum albumin.
Cell Separation Process The cell separation process can be done via a column-based device as follows (FIG. 4A):
a) add 1 mL 1× Cell Separation Buffer to equilibrate a column having a mesh with a pore size range of 10-100 μm;
b) load the streptavidin-conjugated alginate hydrogel microbeads-antibody-cells complex into the column and collect the flow-through unbound cells;
c) wash the column using 1× Cell Separation Buffer and collect all the samples from washing step; and
d) dissolve the particles for 5 min by adding 1× Cell Release Buffer and collect all the bound cells from this elution step for further applications. The Cell Release Buffer is a pH 7.4 salt solution containing a chelating agent. This solution contains 25 mM HEPES, 137 mM NaCl, 2.7 mM KCl, 2 mM EDTA, and 0.5% w/v bovine serum albumin.

Figure 4B:
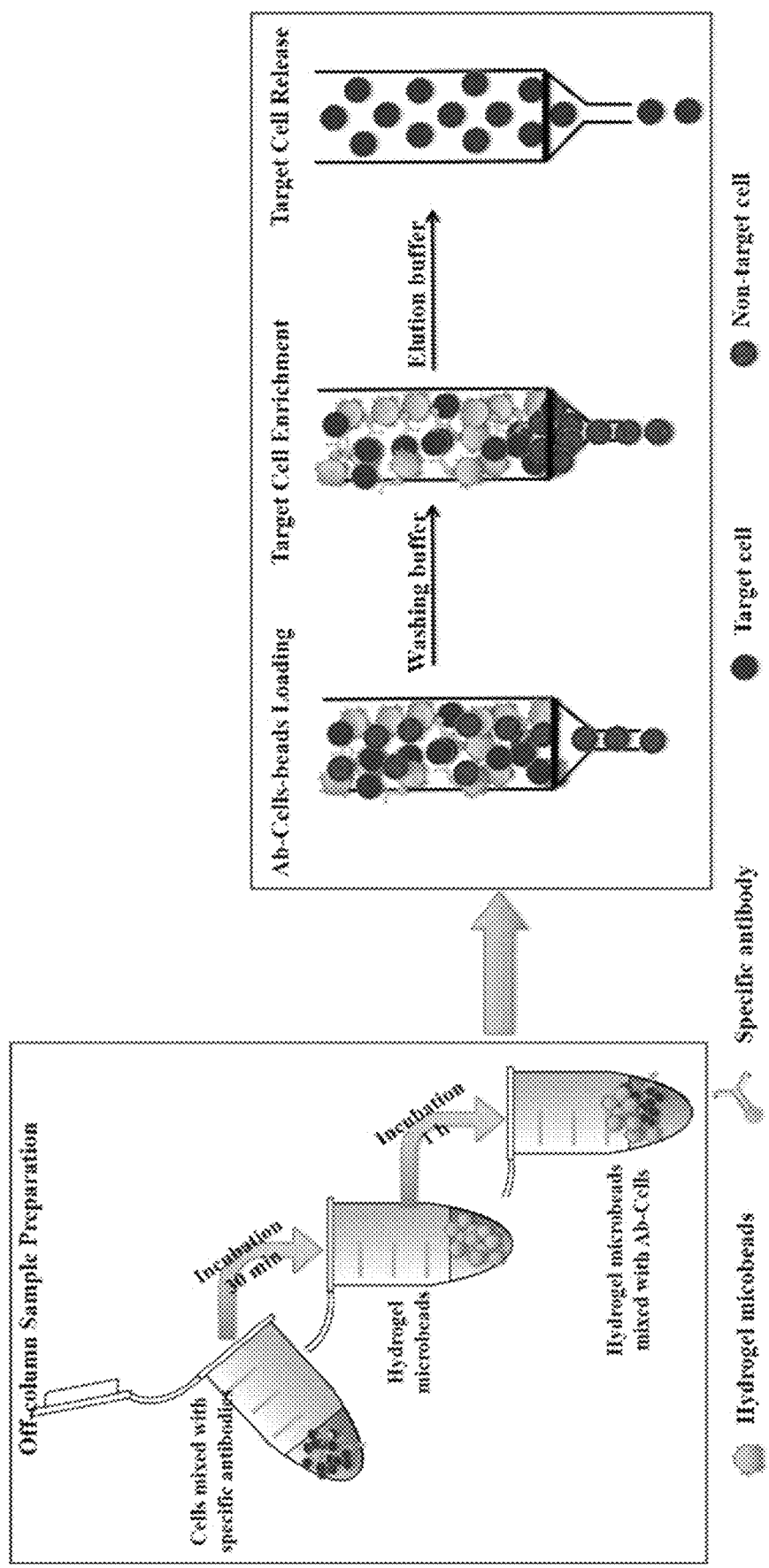

The cell separation process can also be done via a strainer-based device as follows (FIG. 4B):
a) attach the strainer with a mesh pore size range of 10-100 μm to a 50 mL centrifuge tube and add 1 mL 1× Cell Separation Buffer to equilibrate the strainer;
b) pour streptavidin-conjugated alginate hydrogel microbeads-antibody-cells complex onto the strainer. Unbound cells run through the strainer into the centrifuge tube, and the bead-bound target cells remain on the strainer;
c) wash the strainer sufficiently by adding 1× Cell Separation Buffer, and the bead-bound target cells will stay on the strainer;
d) invert the strainer and attach it to a new 50 mL centrifuge tube, then add sufficient 1× Cell Release Buffer onto the strainer to dissolve the beads completely. The released purified target cells in the tube are now ready for further use.

For the hydrogel particles to be used for separation experiments, a barrier is required to separate non-target from target cells. In a positive selection configuration, non-target cells are washed off and/or fall through and are discarded. Subsequent addition of chelating agent and/or elution buffer dissolves particles, releasing target cells which in turn pass through porous barrier for collection. Gravity driven flow is used to move cells through porous barrier, however other methods could be used—e.g. centrifugation, gas pressure, or fluidics.

Example 3

Sodium alginate was chemically cross-linked to 4-arm PEG amine using calcium ions to form hydrogel microbeads which were subsequently functionalized with streptavidin. Various formulations of the hydrogel were possible by varying both the quantity and ratios of the following ingredients. Variation of these quantities and ratios influenced the viscosity, viscoelasticity, and particle size of the resulting hydrogel microbeads. Hydrogel microbeads were produced in a broad range of sizes, using two primary particle production methods. The first method was using a spray apparatus (as described herein) and the second, an aerodynamically assisted jet spray using a commercially available Nisco VAR J30 encapsulator system. Table 1 provides components for various substrates of the invention. Table 2 provides exemplary parameters for formation of various substrates of the invention. A hardening solution of 1 L 70% Isopropyl alcohol with 100 mM $CaCl_2$ was employed with the processes summarized in Table 2.

TABLE 1

Experimental compositions of various hydrogels

| | Hydrogel 1 | Hydrogel 2 | Hydrogel 3 | Hydrogel 4 |
|---|---|---|---|---|
| [Sodium alginate] | 450 mg | 450 mg | 900 mg | 900 mg |
| [4-arm PEG] | 225 mg | 225 mg | 450 mg | 450 mg |
| [sulfo-NHS] | 22 mg | 22 mg | 44 mg | 44 mg |

TABLE 1-continued

Experimental compositions of various hydrogels

|  | Hydrogel 1 | Hydrogel 2 | Hydrogel 3 | Hydrogel 4 |
|---|---|---|---|---|
| [EDC] | 8 mg | 8 mg | 16 mg | 16 mg |
| [PEG4-SPDP] | 100 mg | 200 mg | 100 mg | 200 mg |
| [Water] | 30 mL | 30 mL | 30 mL | 30 mL |

TABLE 2

Process parameters used to produce hydrogel microbeads

| | Equipment (Nozzle) | Particle Size (μm) | Hydrogel used | Air Pressure | Pump/Flow Rate (mL/min) | Spray Distance | Stir Speed |
|---|---|---|---|---|---|---|---|
| 1 | spray apparatus | 10-150 | 1 or 2 | 10 psi | 1 | 40 cm | 200 rpm |
| 2 | spray apparatus | 10-200 | 3 or 4 | 5 psi | 1 | 40 cm | 200 rpm |
| 3 | Nisco (150 μm) | 100-150 | 3 or 4 | 500 mBar | 1.5 | 17 cm | 200 rpm |
| 4 | Nisco (150 μm) | 150-200 | 3 or 4 | 250 mBar | 1.5 | 17 cm | 200 rpm |
| 5 | Nisco (150 μm) | 15-50 | 1 or 2 | 500 mBar | 0.5 | 22.5 cm | 200 rpm |
| 6 | Nisco (150 μm) | 50-100 | 1 or 2 | 500 mBar | 1 | 22.5 cm | 200 rpm |

Prior to conjugating streptavidin to hydrogel microbeads, addition of thiol-groups to unsprayed hydrogel or hydrogel microbeads was first performed via addition of PEG4-SPDP. 100 mg PEG4-SPDP was added into 30 mL of either hydrogel or hydrogel particle solution in HEPES buffered saline with 20 mM $CaCl_2$) (pH 7.4), and the mixture was shaken at room temperature for 2 h (or overnight) to produce thiol-hydrogel or thiol-hydrogel microbeads. 114 mg Tris (2-carboxyethyl)phosphine hydrochloride (TCEP-HCl) was then added into 20 mL thiol-hydrogel microbead solution for 2 h to form reduced thiol-groups. Streptavidin maleimide activation was performed using sulfosuccinimidyl-4-(N-maleimidomethyl)cyclohexane-1-carboxylate (Sulfo-SMCC). 9.6 mg Sulfo-SMCC was mixed with 200 mg streptavidin in 20 mL 1×PBS buffer, and the mixture was shaken at room temperature for 30 min to produce maleimide-activated streptavidin. After buffer exchange with HEPES buffered saline with 20 mM $CaCl_2$) (pH 7.4), approximately 250 mg of reduced thiol-particles was mixed with 200 mg maleimide-activated streptavidin in 20 mL HEPES buffered saline with 20 mM $CaCl_2$) pH7.4, and the mixture was shaken at room temperature for 2 h (or overnight) to produce streptavidin-conjugated hydrogel microbeads. The final streptavidin-conjugated hydrogel microbeads were stored at 4° C. in HEPES buffered saline with 20 mM $CaCl_2$) and 0.09% (w/v) sodium azide (pH 7.4).

Example 4

In this example, targeted groups of cells were captured and released. For example, CD34+ Kg1A cells have been captured and release; CD4+ T cells have been captured directly from PBMC; and CD4+ and CD8+ T cells have been separated from a CD3+ T cell population. A summary of the starting experimental conditions for this example is provided in Table 3.

TABLE 3

Cell separation experiments performed using a device of the invention, including target cell types, starting cell numbers and cell binding markers

| | Starting cell type | Target cell type | Starting cell number/s | Separation target/s |
|---|---|---|---|---|
| Example A | Kg1A (bone marrow acute myelogenous leukemia) | Kg1A | at least 1 million | CD34 |
| Example B | Peripheral blood mononuclear cells (PBMC) | CD3+ T cells | at least 1 million | CD3 |
| Example C | Peripheral blood mononuclear cells (PBMC) | CD4+ T cells | at least 1 million | CD4 |
| Example D | Peripheral blood mononuclear cells (PBMC) | CD8+ T cells | at least 1 million | CD8 |
| Example E | CD3+ T Lymphocytes | CD4+ T cells | at least 1 million | CD4 |
| Example F | CD3+ T Lymphocytes | CD8+ T cells | at least 1 million | CD8 |

Following the separation procedures previously outlined, capture and release of Kg1A cells (bone marrow acute myelogenous leukemia) via biotinylated anti-human CD34 antibody (clone 581) using streptavidin-conjugated hydrogel microbeads through both column-based and cell strainer-based devices resulted in high cell uptake rate of 92% and high cell recovery rate of 86%; this is shown in the histogram plots of FIGS. 6A-6B. This effectively demonstrates the high sensitivity and high binding efficiency of streptavidin-conjugated hydrogel particles of the present invention.

Alginate hydrogel microbeads and a strainer-based device were used in the isolation and purification of CD4+ T cells using a biotinylated anti-human CD4 antibody (clone RPA-T4) attached to the microbeads, resulting in excellent capture of the desired CD4+ T-Cells in the initial PBMC sample. The results of this experiment are shown in FIGS. 7A-7C, with flow cytometry data indicating a high purity of cellular isolation at 96.3%. These cells were found to have higher viability (at 99.2%) after separation than those in the original PBMC sample. A subsequent experiment aimed at isolating and purifying CD8+ T-Cells using a biotinylated-anti-CD8 antibody (clone RPA-T8), starting with a homogeneous population of CD3+T Lymphocytes, resulted in high purity at 98% and higher viability at 97% after separation, with the results of this experiment shown in FIGS. 8A-8C.

In the provided examples, using a device of the invention, high purity cell separation was accomplished with full retention of cell viability and function as demonstrated by flow cytometric analysis to establish purity and viability of separated cells and assess the efficiency of the cell separation. All results obtained above indicate the high efficiency and high selectivity of the hydrogel microbeads of the invention, resulting in an innovative and more effective approach to cell separation at different scales, Other embodiments are in the claims.

What is claimed is:

1. A composition comprising a plurality of hydrogel microbeads, each covalently attached to a binding unit configured to bind a surface of a target cell, wherein the hydrogel microbeads comprise an alginic acid-polyethylene glycol (PEG) copolymer and a crosslinking agent, wherein the crosslinking agent is a cation, wherein the hydrogel microbeads have a diameter from about 1-1000 μm, and wherein all of the hydrogel microbeads liquefies upon decreased availability of the crosslinking agent.

2. The composition of claim 1, wherein the hydrogel has a median viscosity of between about 0.01 and 400 centipoise (cP).

3. The composition of claim 2, wherein the hydrogel has a median viscosity of about 80 cP.

4. The composition of claim 1, wherein the microbeads have a polydispersity index of 1-2.

5. The composition of claim 1, wherein the binding unit is attached to the surface of the microbeads.

6. The composition of claim 5, wherein the binding unit comprises an antibody or antigen-binding fragment thereof, biotin, or a biotin binding protein.

7. The composition of claim 6, wherein the binding unit comprises an antibody or antigen-binding fragment thereof, and wherein the antibody or antigen binding fragment thereof is a monoclonal antibody or antigen-binding fragment thereof, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv')2) molecule, a domain antibody, a diabody, a triabody, an affibody, a domain antibody, a SMIP, a nanobody, a Fv fragment, a Fab fragment, a F(ab')2 molecule, or a tandem scFv (taFv) fragment.

8. The composition of claim 1, wherein the binding unit binds one or more cell surface molecules selected from the group consisting of T cell receptor (TCR), CD3, CD4, CD8, CD11a, CD11b, CD11c, CD14, CD15, CD16, CD19, CD25, CD33, CD34, CD45RO, CD56, major histocompatibility complex (MHC), and chimeric antigen receptor (CAR).

9. The composition of claim 1, wherein the cation is $Mg^{2+}$, $Ca^{2+}$, $Sr^{2+}$, $Ba^{2+}$, $Zn^{2+}$, $Cu^{2+}$, or $Al^{3+}$.

10. The composition of claim 9, wherein the cation is $Ca^{2+}$.

11. A device comprising a container comprising an inlet and an outlet, the container containing a porous substrate and being configured to permit passage of cells from the inlet through the outlet while retaining the porous substrate within the container, wherein a binding unit configured to bind a surface of a target cell is covalently attached to the porous substrate, wherein the porous substrate comprises hydrogel microbeads, wherein the hydrogel microbeads comprise an alginic acid-polyethylene glycol (PEG) copolymer and a crosslinking agent, wherein the crosslinking agent is a cation, wherein the hydrogel microbeads have a diameter from about 1-1000 μm, and wherein all or a portion of the porous substrate liquefies upon decreased availability of the crosslinking agent.

12. The device of claim 11, further comprising one or more additional containers operatively connected to the outlet, wherein the one or more additional containers each comprises the same or different binding unit.

13. The device of claim 12, further comprising one or more three-way valves.

14. A kit comprising the composition of claim 1 and a strainer through which cells can pass but liquified substrate from liquification of said hydrogel microbeads cannot.

15. The kit of claim 14, wherein the strainer comprises a mesh or sieve.

16. The kit of claim 15, wherein the strainer has a pore size of 1-1000 μm.

17. The composition of claim 1, wherein the PEG is a branched 4-armed PEG.

* * * * *